(12) United States Patent
Quintero et al.

(10) Patent No.: US 10,945,720 B2
(45) Date of Patent: Mar. 16, 2021

(54) SYSTEMS AND METHODS FOR CLOSING INCISIONS FORMED IN FRAGILE TISSUE

(71) Applicant: Ethicon, Inc., Somerville, NJ (US)

(72) Inventors: Julian Quintero, Flemington, NJ (US); Leo B. Kriksunov, Ithaca, NY (US); Shane A. Lacy, Bound Brook, NJ (US); Ibraheem T. Badejo, Natick, MA (US)

(73) Assignee: Ethicon, Inc., Somerville, NJ (US)

( * ) Notice: Subject to any disclaimer, the term of this patent is extended or adjusted under 35 U.S.C. 154(b) by 428 days.

(21) Appl. No.: 15/703,344

(22) Filed: Sep. 13, 2017

(65) Prior Publication Data

US 2019/0076140 A1    Mar. 14, 2019

(51) Int. Cl.
*A61B 17/04* (2006.01)
*A61B 17/08* (2006.01)
*A61B 17/06* (2006.01)
*A61B 46/20* (2016.01)

(52) U.S. Cl.
CPC .......... *A61B 17/0466* (2013.01); *A61B 17/04* (2013.01); *A61B 17/085* (2013.01); *A61B 17/06166* (2013.01); *A61B 2017/0495* (2013.01); *A61B 2017/081* (2013.01); *A61B 2046/205* (2016.02)

(58) Field of Classification Search
CPC ... A61B 17/0466; A61B 17/085; A61B 17/04; A61B 17/06166; A61B 2017/081; A61B 2017/0495; A61B 2046/205
See application file for complete search history.

(56) References Cited

U.S. PATENT DOCUMENTS

| 3,376,869 | A | | 4/1968 | Botysko | |
|---|---|---|---|---|---|
| 4,531,521 | A | | 7/1985 | Haverstock | |
| 4,584,192 | A | | 4/1986 | Dell et al. | |
| 4,899,762 | A | * | 2/1990 | Muller | A61B 17/085 128/850 |
| 4,966,605 | A | * | 10/1990 | Thieler | A61B 17/085 606/215 |

(Continued)

FOREIGN PATENT DOCUMENTS

EP    0436852    7/1991

OTHER PUBLICATIONS

International Search Report issued in corresponding International Application No. PCT/US2018/056939, dated Dec. 4, 2018, 5 pages.

*Primary Examiner* — Anh T Dang

(57) ABSTRACT

A method of reinforcing subcutaneous fragile tissue includes obtaining an absorbable surgical mesh having top and bottom major surfaces, the absorbable surgical mesh including a stitching zone and first and second reinforcing zones that bound opposite sides of the stitching zone. The method includes making an incision in a patient's skin for exposing subcutaneous fragile tissue, using one or more absorbable adhesives for adhering the bottom major surface of the absorbable surgical mesh to the subcutaneous fragile tissue, creating an incision through the stitching zone of the absorbable surgical mesh and into the subcutaneous fragile tissue, performing a surgical procedure through the incision, and passing an absorbable suture through the stitching zone of the absorbable surgical mesh and the fragile tissue for closing the incision.

20 Claims, 8 Drawing Sheets

(56) References Cited

U.S. PATENT DOCUMENTS

| | | | |
|---|---|---|---|
| 5,730,994 | A | 3/1998 | Askill et al. |
| 5,855,208 | A | 1/1999 | Askill et al. |
| 5,947,917 | A | 9/1999 | Carte et al. |
| 5,979,450 | A | 11/1999 | Baker et al. |
| 6,139,856 | A | 10/2000 | Kaminska et al. |
| 6,664,309 | B2 | 12/2003 | Svenningsen et al. |
| 6,742,522 | B1 | 6/2004 | Baker et al. |
| 8,061,917 | B2 | 11/2011 | Stenton et al. |
| 8,609,128 | B2 | 12/2013 | Zhang et al. |
| 8,777,986 | B2 | 7/2014 | Straehnz et al. |
| 2007/0021655 | A1* | 1/2007 | Sayeg .................. A61B 17/02 600/210 |
| 2012/0095502 | A1 | 4/2012 | Bargon et al. |
| 2012/0222686 | A1 | 9/2012 | Lockwood et al. |
| 2013/0239977 | A1 | 12/2013 | McGuire |
| 2014/0261454 | A1 | 9/2014 | Dokken et al. |
| 2018/0030321 | A1* | 2/2018 | Tunius .................. C08G 18/10 |

\* cited by examiner

SYSTEMS AND METHODS FOR CLOSING INCISIONS FORMED IN FRAGILE TISSUE

BACKGROUND OF THE INVENTION

Field of the Invention

The present patent application is generally related to surgical instruments and procedures, and is more specifically related to closing surgical incisions and wound closure systems.

Description of the Related Art

During a surgery, a surgical incision is a cut made through the skin and/or soft tissue to facilitate an operation or procedure. In many instances, multiple incisions may be necessary. In general, a surgical incision is made as small and unobtrusive as possible to facilitate safe and timely operating conditions.

At the end of a surgical procedure, the surgical incisions must be closed. Over the years, many different techniques have been developed for closing surgical incisions. One widely used technique involves using sutures having a single knot or a series of knots. In recent years, absorbable sutures and barbed sutures have been used for closing surgical incisions. In addition, surgical tacks have been used for closing surgical incisions, which reduces the amount of time required for closing incisions.

Some technical advances have been directed to closing surgical incisions without using sutures or surgical tacks. For example, commonly assigned U.S. Pat. No. 8,777,986 to Straehnz et al. discloses an incision guide and wound closure device including a surgical mesh having a top surface and a bottom surface, and first and second incision guides affixed to the top surface of the surgical mesh. The bottom surface of the mesh is adhered to tissue using clear or translucent adhesive. The first and second incision guides have opposing alignment surfaces that are adapted to guide a cutting instrument for making an incision through the mesh and into the tissue. The device has a closing element that is moveable along the length of the respective first and second incision guides for drawing the first and second alignment surfaces toward one another for closing the incision opening in the tissue.

Most of the technological developments related to closing incisions have been directed to closing incisions formed in the outermost skin layers of patients. The outer skin layer is relatively rugged and using sutures, staples or tacks to close incisions in outer skin layers has proven to be safe and effective.

In contrast, the repair of subcutaneous fragile body tissue, such as the liver and spleen, has always been a difficult problem for surgeons because attempts to suture fragile tissue frequently results in the suture tearing out. The cross-sectional area of the suture is so small that the force applied by the surgeon to position and tie the suture tends to cut through the fragile tissue that is being repaired. Even in instances where the surgeon may succeed in placing the sutures without undue damage to the fragile tissue, the sutures may tear out before healing is complete.

FIG. 7 shows a prior art method used for suturing fragile tissue 10. After an incision 14 is formed in the fragile tissue 10 for performing a surgical procedure, the incision 14 is closed using a surgical closing device such as a suture 16. Because of the friable nature of the fragile tissue 10, the suture 16 may tear through the fragile tissue, thereby preventing the incision 14 from being properly closed.

In response to the above-noted problems associated with suturing fragile tissue, some surgeons began to use sheets of fascia lata, an absorbable material that is derived from animal sources. The sheets of fascia lata were used to hold the suture in place until complete healing of the fragile tissue. Unfortunately, thin sheets of fascia lata exhibit poor tear strength and the lack of uniformity of the sheets leaves much to be desired.

One solution directed to manufacturing a man-made film for use when closing incisions formed in fragile tissue is disclosed in commonly assigned U.S. Pat. No. 3,376,869 to Borysko. In one embodiment, the '869 patent teaches how to make a surgical collagen film by extruding a homogenous dispersion of pure swollen collagen fibrils into a dehydrating bath to form a multi-filament tape. The multi-filament tape is cut to various lengths and placed on a suitable support such as a screen to build up a layer of collagen filaments that are randomly aligned in planes parallel to the surface of the supporting screen. The layer of collagen monofilaments is laminated and bonded together into a unitary structure by immersing the collagen layer and its supporting screen in a dilute aqueous acid solution, which produces a film having improved tear strength that may be used for suturing fragile tissue.

In spite of the above advances, there remains a need for improved systems, devices and methods for safely and effectively closing incisions made in fragile tissue, such as subcutaneous fragile tissue.

SUMMARY OF THE INVENTION

In one embodiment, prior to making an incision in fragile tissue, such as subcutaneous fragile tissue, a reinforcing incision drape is placed on top of the fragile tissue. In one embodiment, the reinforcing incision drape includes an absorbable surgical mesh that may be secured directly on the surface of the fragile tissue using one or more adhesives disposed on the reinforcing incision drape. In one embodiment, the reinforcing incision drape may include a weaker adhesive (e.g., a pressure sensitive adhesive) located on the wound-facing side of drape. In one embodiment, prior to making an incision through the reinforcing incision drape, the drape may be attached to the fragile tissue using a second, stronger adhesive (e.g., a rapidly cross-linking adhesive such as cyanoacrylate) to form a reinforced incision drape that is a composite of the drape and the hardened adhesive. In one embodiment, after the reinforcing incision drape is adhered to the fragile tissue, an incision is made through the reinforced incision drape. After the surgical procedure has been completed, suture stitches may be applied directly through the reinforced incision drape that is adhered to the fragile tissue. The reinforced incision drape preferably supports the fragile tissue during healing and prevents the sutures from tearing out of the fragile tissue prior to complete healing of the fragile tissue.

In one embodiment, the reinforcing incision drape preferably has a distinct stitching zone located in a central portion of the drape, where sutures are passed through the drape, and first and second reinforcing zones that surround opposite sides of the centrally located stitching zone. In one embodiment, the first and second reinforcing zones preferably form peripheral portions of the reinforcing incision drape. In one embodiment, the stronger adhesive is used for bonding the first and second reinforcing zones to the fragile tissue and the weaker adhesive is used for adhering the stitching zone to the fragile adhesive.

In one embodiment, the first and second reinforcing zones preferably have different structural properties than the stitching zone. In one embodiment, the first and second reinforcing zones are more porous than the stitching zone. In one embodiment, the stitching zone portion of the reinforcing incision drape is non-porous and has no cross-linking initiator (e.g., cyanoacrylate). In one embodiment, the stitching zone portion of the reinforcing incision drape is porous with higher porosity than the rest of the mesh and has no cross-linking initiator. In one embodiment, the stitching zone portion of the reinforcing incision drape is less porous than the rest of the mesh and has no cross-linking initiator.

In one embodiment, the stitching zone of the reinforcing incision drape is attached to the fragile tissue using only by a weaker adhesive (e.g., a pressure sensitive adhesive), and not by using a stronger liquid adhesive (e.g., a rapidly cross-linking adhesive such as cyanoacrylate), which results in easier needle penetration through the stitching zone and faster tissue healing. In one embodiment, the first and second reinforcing zones are attached to the fragile tissue using at least a stronger adhesive, and optionally with both the weaker adhesive for initial placement of the drape and the stronger adhesive for a more permanent placement of the drape.

In one embodiment, the stitching zone may be covered by a removable liner, which is disposed on a top surface of the reinforcing incision drape that is opposite to the wound-facing side of the drape. The removable liner preferably remains in place over the stitching zone prior to and/or during application of the stronger adhesive, thereby serving as a mask to prevent the stronger adhesive from contacting the stitching zone. After the stronger adhesive has been applied over the reinforcing zones of the drape, the liner may be removed to expose the top surface of the stitching zone so that an incision may be made through the stitching zone.

In one embodiment, the removable liner may have laterally extending strips that extend through the first and second reinforcing zones. The laterally extending strips may mask sections of the first and second reinforcing zones from coming in contact with the second, stronger adhesive. The liner and the laterally extending strips may be removed from the top surface of the reinforcing incision drape for being discarded after the application of the stronger adhesive.

In one embodiment, the reinforcing incision drape may have a plurality of large openings that are located in the first and second reinforcing zone areas covered by the laterally extending strips. The large openings are preferably significantly larger than the pores located within the first and second reinforcing zones. After application of the stronger, second adhesive and removal of the releasable liner and the laterally extending strips, the openings desirably provide for areas of fragile tissue that are not covered by the reinforcing incision drape or the adhesive.

In one embodiment, a tissue reinforcing system may include a tissue adhesive that is absorbable or non-absorbable. In one embodiment, the tissue adhesive may be monomeric or polymeric with a viscosity of between about 10-500 cP. In one embodiment, a system for treating fragile tissue desirably includes a reinforcing incision drape, such as an absorbable or non-absorbable surgical mesh. In one embodiment, a surgical mesh preferably has fibers that are oriented and that have a structure that allows for more elasticity parallel to the direction of a surgical incision and less elasticity perpendicular to the direction of a surgical incision.

In one embodiment, an adhesive (with or without an initiator, activator, or the like) is applied over fragile tissue where a surgical incision will be created. In one embodiment, prior to the adhesive hardening, a surgical mesh (with or without an initiator, activator, or the like) is preferably applied over the unhardened adhesive to ensure proper integration of the adhesive and the surgical mesh. In one embodiment, after the surgical mesh has been positioned over the fragile tissue, additional adhesive may be applied to the mesh to enhance adherence of the mesh to the fragile tissue.

In one embodiment, upon hardening of the adhesive/surgical mesh composite, a surgical incision may be created through adhesive/mesh composite utilizing surgical tools such as a scalpel. At the time of incision closure, a closing component such as a barbed suture, a traditional braided or monofilament suture, a fastener and/or staples may be used to approximate and close the incision.

In one embodiment, fragile tissue is reinforced by using absorbable adhesive and attaching a reinforcing incision drape or surgical mesh layer to the fragile tissue via absorbable adhesive. In one embodiment, an incision is made though the reinforced tissue (i.e., reinforced by the drape and the adhesive) to perform surgical procedures, and the incision is closed with sutures, whereby the fragile tissue is reinforced by the drape/adhesive composite for resisting cheese-wiring or tearing of the fragile tissue by the sutures.

In one embodiment, a method of reinforcing subcutaneous fragile tissue to avoid "cheese-wiring" during suturing of the fragile tissue includes applying a bioabsorbable adhesive to the fragile tissue, and prior to the absorbable adhesive hardening, applying a reinforcing incision drape such as an absorbable mesh/buttress/pledget/porous fabric/nonwoven on top of the adhesive, for adhering the reinforcing incision drape to the fragile tissue with the adhesive. In one embodiment, more absorbable adhesive may be added on top of the reinforcing incision drape, wherein the composite reinforcing incision drape includes a combination of the reinforcing incision drape and the hardened absorbable adhesive.

In one embodiment, a surgical incision may be created through the reinforcing incision drape and the hardened adhesive. After the incision is made, a surgical procedure is preferably performed through and/or within the incision. At the completion of the surgical procedure, the incision is preferably closed using a surgical closure component, such as a regular suture, a barbed suture, an absorbable suture, staples, fasteners, and/or surgical adhesives.

In one embodiment, a method of reinforcing subcutaneous fragile tissue preferably includes obtaining a reinforcing incision drape having top and bottom major faces, and using an adhesive for adhering the bottom major face of the reinforcing incision drape to subcutaneous fragile tissue. In one embodiment, the method preferably includes creating an incision through the reinforcing incision drape and into the subcutaneous fragile tissue, performing a surgical procedure through the incision, and passing a surgical closing component through the reinforcing incision drape and the fragile tissue for closing the incision.

In one embodiment, the reinforcing incision drape, the adhesive, and the surgical closing component are absorbable. In one embodiment, the adhesive may include a weaker adhesive (e.g., a pressure sensitive adhesive) and a stronger adhesive (e.g., a rapidly cross-linking adhesive such as cyanoacrylate).

In one embodiment, the reinforcing incision drape preferably includes an absorbable surgical mesh, the adhesive preferably includes absorbable adhesive, and the surgical closing component preferably includes an absorbable suture.

In one embodiment, the reinforcing incision drape desirably has a centrally located stitching zone, and first and second reinforcing zones that extend along opposite sides of the centrally located stitching zone. In one embodiment, the centrally located stitching zone preferably has different structural properties than the first and second reinforcing zones. In one embodiment, the first and second reinforcing zones are more porous than the centrally located stitching zone.

In one embodiment, the using an adhesive step may include using a weaker adhesive for securing the centrally located stitching zone to the subcutaneous fragile tissue, and using a stronger adhesive for securing the first and second reinforcing zones to the subcutaneous fragile tissue. In one embodiment, the stronger adhesive preferably includes an absorbable adhesive containing a cross-linking initiator, such as cyanoacrylate.

In one embodiment, after the using a weaker adhesive step, the stronger adhesive is applied over the top surface of the reinforcing incision drape and within the first and second reinforcing zones of the reinforcing incision drape. In one embodiment, the bond between the first and second reinforcing zones and the fragile tissue is stronger than the bond between the centrally located stitching zone and the fragile tissue.

In one embodiment, the method may include obtaining a releasable liner over the top surface of the reinforcing incision drape within the stitching zone of the reinforcing incision drape, whereby the releasable liner covers the stitching zone during the applying the stronger adhesive step to prevent the stronger adhesive from contacting the stitching zone. In one embodiment, after the stronger adhesive is applied, the releasable liner may be removed from the top surface of the reinforcing incision drape for exposing the stitching zone at the top surface of the reinforcing incision drape.

In one embodiment, the creating an incision step preferably includes forming an incision in the stitching zone of the reinforcing incision drape and the fragile tissue underlying the stitching zone.

In one embodiment, the passing a surgical closure element step desirably includes passing a surgical suture through the stitching zone of the reinforcing incision drape and the fragile tissue underlying the reinforcing incision drape.

In one embodiment, a method of reinforcing subcutaneous fragile tissue preferable includes obtaining an absorbable surgical mesh having top and bottom major surfaces. In one embodiment, the absorbable surgical mesh desirably has a stitching zone and first and second reinforcing zones that bound opposite sides of the stitching zone.

In one embodiment, the method preferably includes making an incision in a patient's skin for exposing subcutaneous fragile tissue, and using one or more absorbable adhesives for adhering the bottom major surface of the absorbable surgical mesh to the subcutaneous fragile tissue.

In one embodiment, the method desirably includes creating an incision through the stitching zone of the absorbable surgical mesh and into the subcutaneous fragile tissue, performing a surgical procedure through the incision, and passing an absorbable suture through the stitching zone of the absorbable surgical mesh and the fragile tissue for closing the incision.

In one embodiment, the step of using one or more absorbable adhesives preferably includes using a weaker absorbable adhesive for adhering the stitching zone of the absorbable surgical mesh to the subcutaneous fragile tissue, and using a stronger absorbable adhesive for adhering the first and second reinforcing zones of the absorbable surgical mesh to the subcutaneous fragile tissue. In one embodiment, the first and second reinforcing zones may include the weaker adhesive.

In one embodiment, the step of using a stronger absorbable adhesive may include, after placing a bottom surface of the absorbable surgical mesh in contact with the subcutaneous fragile tissue, applying the stronger absorbable adhesive over the top major surface of the absorbable surgical mesh and within the first and second reinforcing zones of the absorbable surgical mesh.

In one embodiment, the method may include obtaining a releasable liner that covers the top major surface of the absorbable surgical mesh within the stitching zone, and, after the applying the stronger absorbable adhesive over the top major surface of the absorbable surgical mesh step, removing the releasable liner for uncovering the stitching zone at the top major surface of the absorbable surgical mesh.

In one embodiment, the stitching zone of the absorbable surgical mesh is less porous than the first and second reinforcing zones of the absorbable surgical mesh. In one embodiment, the first and second reinforcing zones of the absorbable surgical mesh are more porous than the stitching zone of the absorbable surgical mesh.

In one embodiment, a reinforcing incision drape for tissue preferably includes an absorbable surgical mesh having top and bottom major surfaces. In one embodiment, the absorbable surgical mesh includes a stitching zone and first and second reinforcing zones that bound opposite sides of the stitching zone.

In one embodiment, the stitching zone may have first structural properties and the first and second reinforcing zones having second structural properties that differ from the first structural properties of the stitching zone.

In one embodiment, a releasable liner covers the top major surface of the absorbable surgical mesh within the stitching zone of the absorbable surgical mesh.

In one embodiment, the releasable liner preferably includes a central section that covers the stitching zone of the absorbable surgical mesh. In one embodiment, the releasable liner may have a series of first laterally extending releasable strips that are spaced from one another and that extend over sections of the first reinforcing zone between the central section of the releasable liner and a first side edge of the absorbable surgical mesh, whereby the top surface of the absorbable surgical mesh that is located within the first reinforcing zone is exposed between the series of first laterally extending releasable strips. In one embodiment, the releasable liner may have a series of second laterally extending releasable strips that are spaced from one another and that extend over the second reinforcing zone between the central section of the releasable liner and a second side edge of the absorbable surgical mesh, whereby the top surface of the absorbable surgical mesh that is located within the second reinforcing zone is exposed between the series of second laterally extending releasable strips.

In one embodiment, the reinforcing incision drape may include a first set of apertures located within the first reinforcing zone of the absorbable surgical mesh that are larger than the pores located within the first reinforcing zone of the absorbable surgical mesh. In one embodiment, the series of first laterally extending releasable strips preferably cover the first set of apertures.

In one embodiment, the reinforcing incision drape may include a second set of large apertures located within the second reinforcing zone of the absorbable surgical mesh that are larger than the pores located within the second reinforcing zone of the absorbable surgical mesh. In one embodiment, the series of second laterally extending releasable strips preferably cover the second set of apertures.

These and other preferred embodiments of the present invention will be described in more detail below.

DETAILED DESCRIPTION OF PREFERRED EMBODIMENTS

Figure 1A:
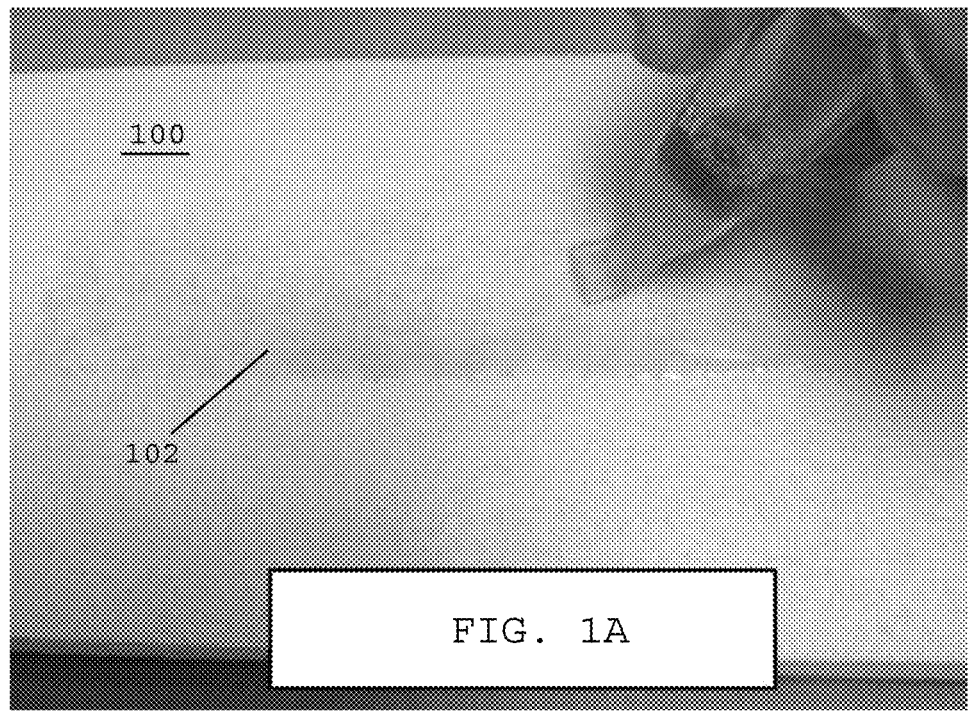
FIG. 1A shows a first step of a surgical procedure during which adhesive is applied over a surface of fragile tissue, in accordance with one embodiment of the present patent application.

Referring to FIG. 1A, in one embodiment, fragile tissue 100, such as subcutaneous fragile tissue, may be prepared for a surgical procedure by applying a layer of a tissue adhesive 102 over an exposed surface of the fragile tissue 100.

Figure 1B:
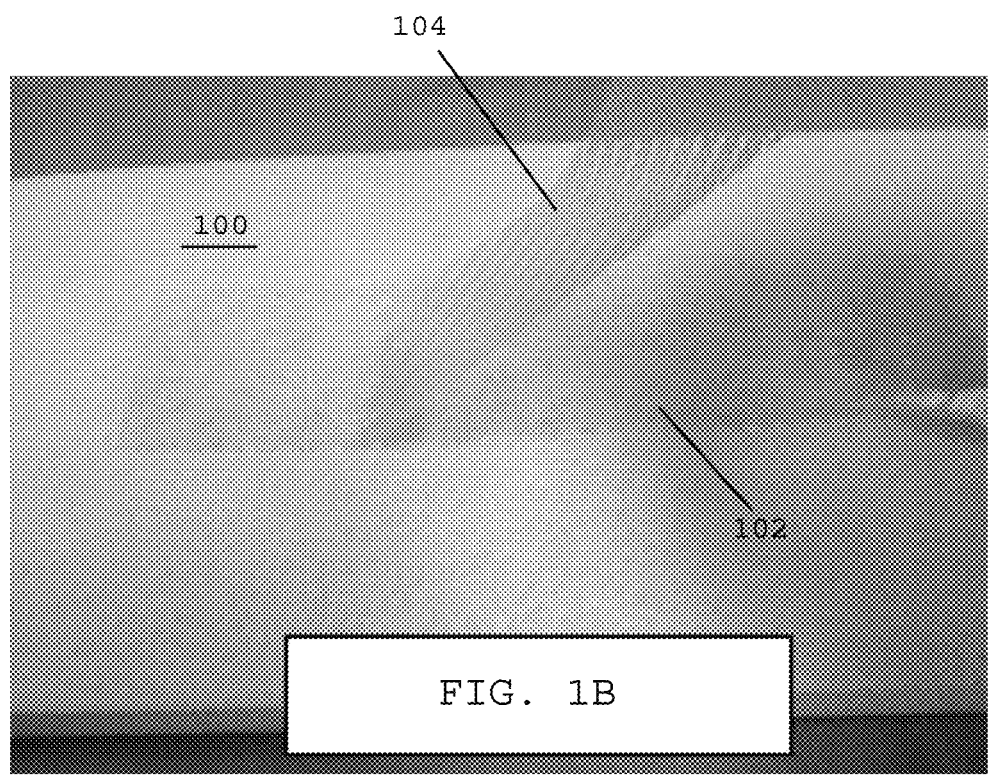
FIG. 1B shows a second step of a surgical procedure during which a reinforcing incision drape is positioned over the adhesive layer and the fragile tissue shown in FIG. 1A, in accordance with one embodiment of the present patent application.

Referring to FIG. 1B, in one embodiment, after the layer of tissue adhesive 102 has been applied to the exposed surface of the fragile tissue 100, a reinforcing incision drape 104 may be positioned on top of the tissue adhesive layer 102. The reinforcing incision drape may be a surgical mesh that is absorbable or non-absorbable.

Figure 1C:
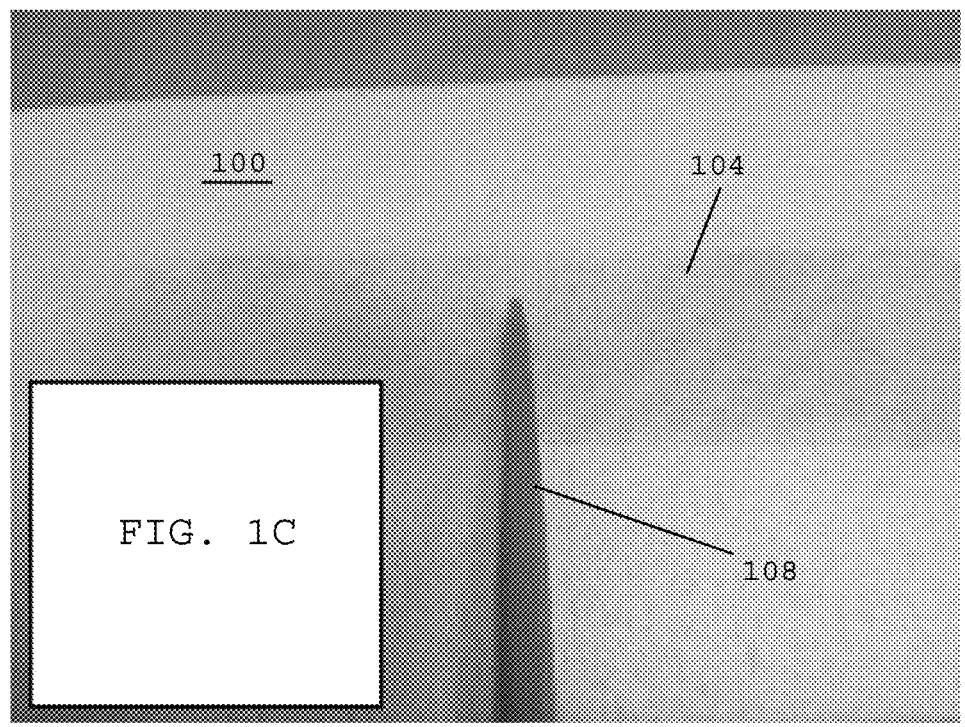
FIG. 1C shows a third step of a surgical procedure during which the reinforcing incision drape is pressed into the adhesive layer shown in FIG. 1A, in accordance with one embodiment of the present patent application.

Referring to FIG. 1C, in one embodiment, a tool 108, such as a prod or rod, may be used for unfurling and/or smoothing out the reinforcing incision drape 104 over the surface of the fragile tissue 100. The tool 108 may also be used to press the reinforcing incision drape 104 into the adhesive tissue layer 102 (FIG. 1B) previously applied to the exposed surface of the fragile tissue 100. In one embodiment, additional tissue adhesive may be applied to the top surface of the deployed reinforcing incision drape 104 to further insure a stable attachment of the reinforcing incision drape to the exposed surface of the fragile tissue 100. In one embodiment, the reinforcing incision drape 104 is porous to allow the additional tissue adhesive to pass therethrough. In one embodiment, the tissue adhesive is initially in liquid form so that it may pass through the drape and hardens as it cures. In one embodiment, the tissue adhesive is allowed to cure and/or harden for reliably securing the reinforcing incision drape 104 in place over the exposed surface of the fragile tissue 100.

Figure 1D:
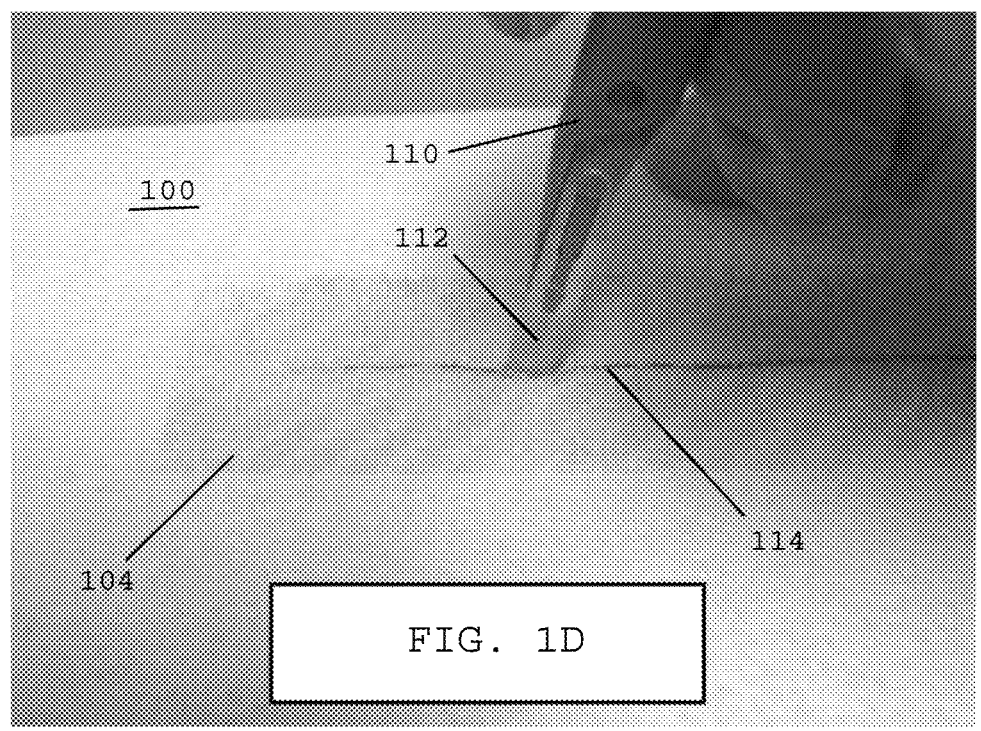
FIG. 1D shows a fourth step of a surgical procedure during which an incision is created in the reinforcing incision drape and into fragile tissue, in accordance with one embodiment of the present patent application.

Referring to FIG. 1D, in one embodiment, a cutting tool 110 having a sharpened cutting blade 112, such as a scalpel, is utilized for creating a surgical incision 114 through the reinforcing incision drape 104, the tissue adhesive layer 102 (FIG. 1B), and the fragile tissue 100. After the surgical incision 114 has been formed, a surgical procedure may be conducted through the wound formed by the incision 114.

Figure 1E:
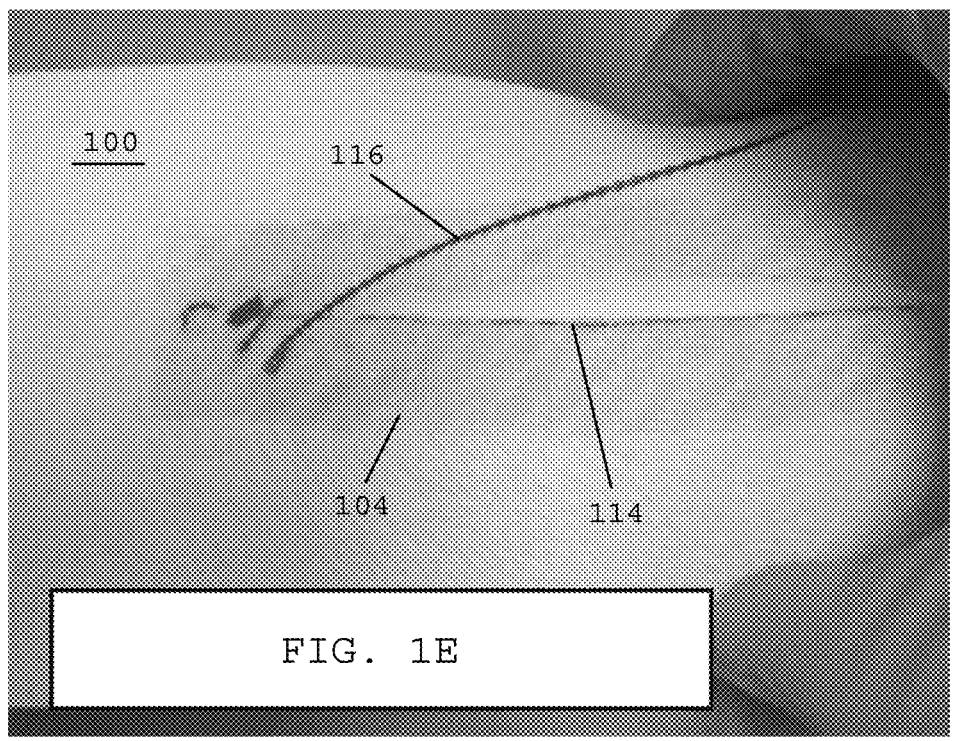
FIG. 1E shows a fifth step of a surgical procedure during which a suture is used to close the incision in the reinforcing incision drape and the fragile tissue, in accordance with one embodiment of the present patent application.

Referring to FIG. 1E, in one embodiment, after a surgical procedure has been completed, a surgical fastening element, such as a suture 116, may be utilized for closing the incision 114 to approximate the opposing edges of the fragile tissue 100 lying on opposite sides of the incision 114, and the opposing cut edges of the reinforcing incision drape 104. The suture 116 is desirably passed through the reinforcing incision drape 104 located on both sides of the incision 114 formed in the reinforcing incision drape for drawing together both the opposing edges of the reinforcing incision drape 104 and the opposing edges of the fragile tissue 100.

In one embodiment, the surgical closure element may be a suture, an absorbable or non-absorbable suture, a barbed suture, surgical staples, and/or surgical adhesives.

Figure 1F:
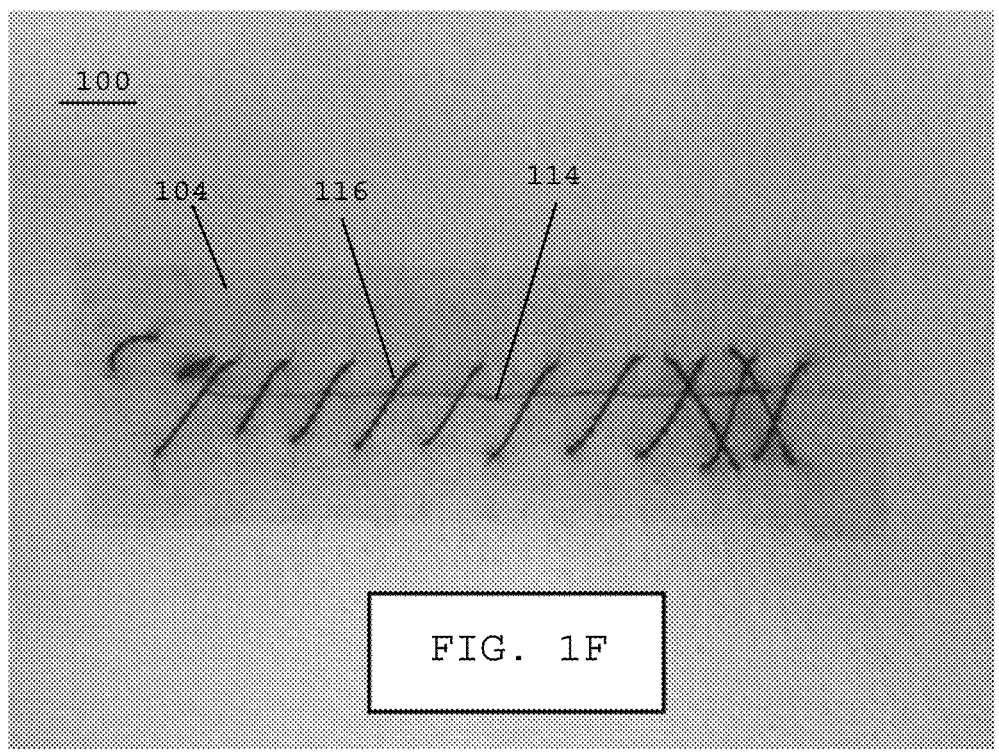
FIG. 1F shows a sixth step of a surgical procedure during which the suture has fully closed the incision in the reinforcing incision drape and the fragile tissue, in accordance with one embodiment of the present patent application.

Referring to FIG. 1F, in one embodiment, the suture 116 preferably passes through the reinforcing incision drape 104 and into the fragile tissue 100 for approximating the opposing edges of the fragile tissue at the incision line 114. In one embodiment, the suture 116, the reinforcing incision drape 104, and the tissue adhesive layer 102 (FIG. 1B) are absorbable so that the components do not have to be removed from a patient after healing of the wound created by the incision 114. The reinforcing incision drape 104 supports the fragile tissue during suturing and healing so that the fragile tissue is not torn by the suture 116.

Figure 2:
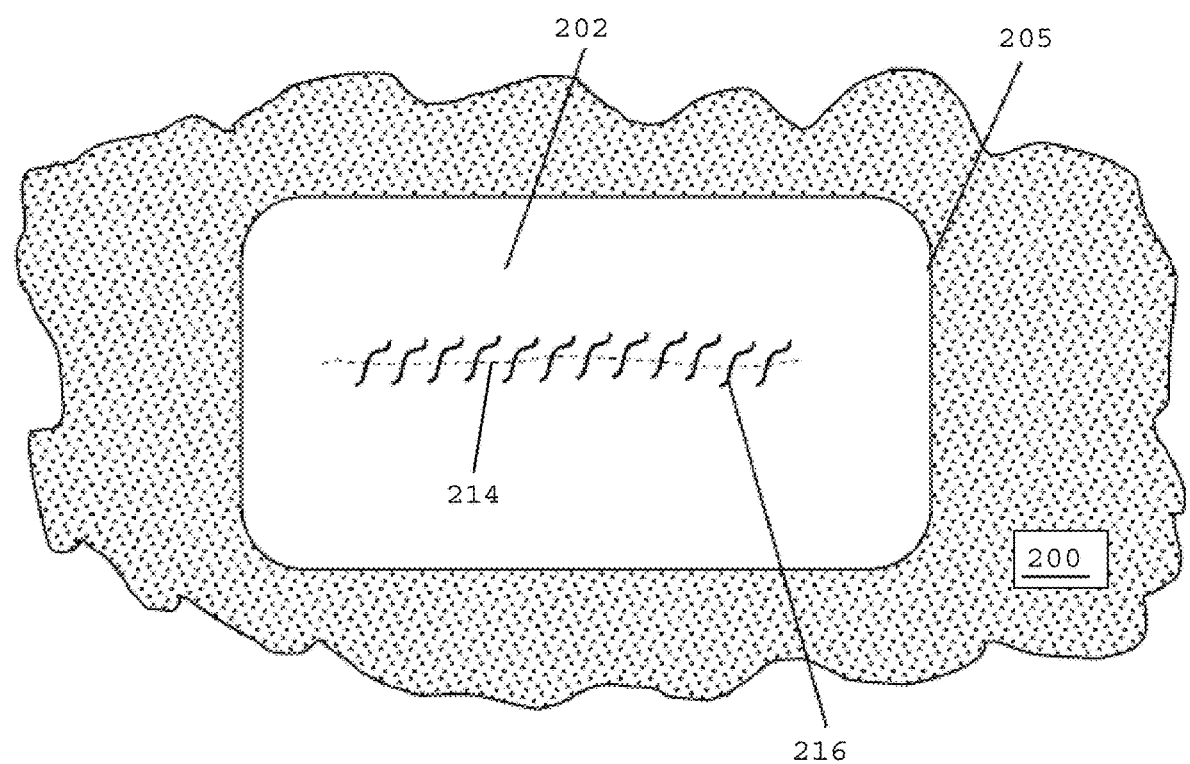
FIG. 2 shows a reinforcing incision drape positioned over fragile tissue, in accordance with one embodiment of the present patent application.

Referring to FIG. 2, in one embodiment, a reinforcing incision drape 202, such as an absorbable, porous surgical mesh, has an outer perimeter 205 that is sized to cover a surgical site located on fragile tissue 200. In one embodiment, the reinforcing incision drape 202 is positioned atop the fragile tissue 200 prior to making an incision in the fragile tissue. In one embodiment, the reinforcing incision drape 202 is positioned directly on an exposed surface of the fragile tissue 200. The reinforcing incision drape 202 may include a porous mesh having a polymerization initiator disposed on the mesh. In one embodiment, the reinforcing incision drape 202 has a pressure sensitive adhesive (PSA) on a wound-facing side of the reinforcing incision drape 202. The PSA is preferably used for initial placement of the drape on the fragile tissue. In one embodiment, after initial placement, the reinforcing incision drape may be attached to the fragile tissue 200 using a second, stronger adhesive (e.g., a rapidly cross-linking adhesive such as cyanoacrylate) to form a reinforced incision drape 202 prior to forming an incision.

In one embodiment, an incision 214 may be created through the reinforcing incision drape 202 and into the fragile tissue 200. After a surgical procedure has been completed through the incision 214, surgical sutures 216 may be applied directly through the reinforcing incision drape 202 that remains attached to the fragile tissue 200. The surgical sutures 216 preferably approximate and/or draw the opposing edges of the cut fragile tissue 200 together, and also desirably draw the opposing cut edges of the reinforcing incision drape 202 together for closing the wound formed by the incision 214. In one embodiment, the reinforcing incision drape 202 is absorbable and is absorbed by a patient's body during and/or after healing of the incision 214. In one embodiment, the suture material 216 is also absorbable. In one embodiment, the pressure sensitive adhesive and the second, stronger adhesive used to more reliably secure the reinforcing incision drape 202 to the fragile tissue 200 is also absorbable.

Figure 3A:
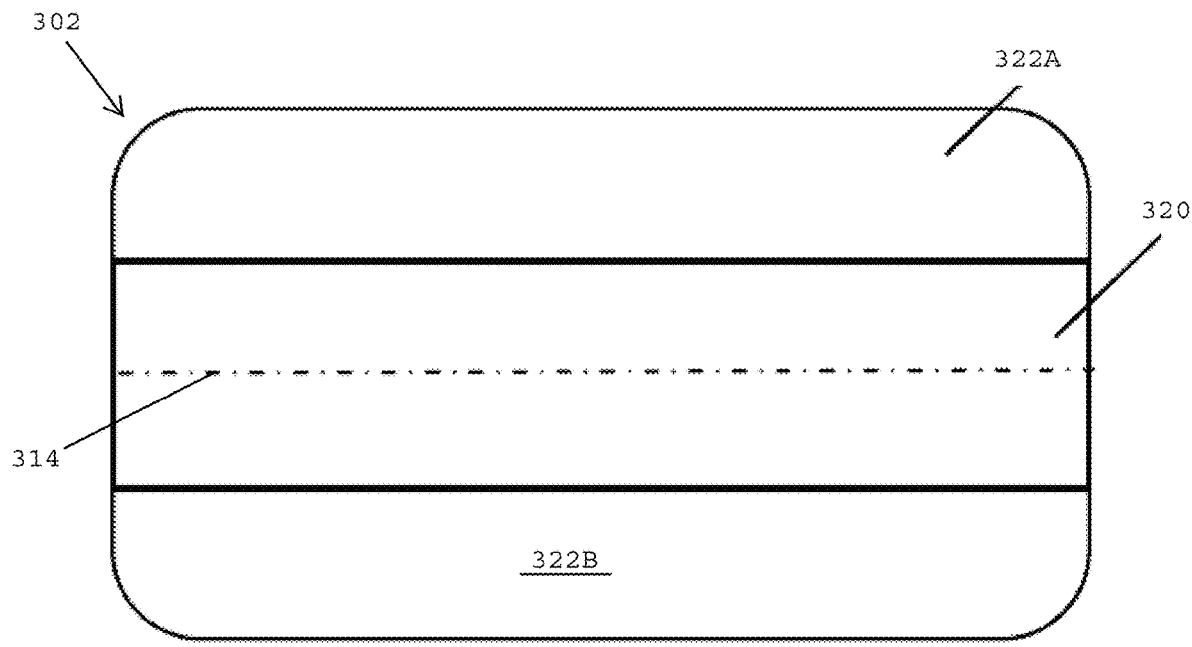
FIG. 3A shows a top plan view of a reinforcing incision drape, in accordance with one embodiment of the present patent application.

Referring to FIG. 3A, in one embodiment, a reinforcing incision drape 302, such as a porous, absorbable surgical mesh, preferably includes a centrally located stitching zone 320 that is bounded on both sides by first and second reinforcing zones 322A, 322B. The stitching zone 320 is adapted to accommodate an incision 314 formed through the reinforcing incision drape 302. The central stitching zone 320 may have different structural properties than the reinforcing zones 322A, 322B. For example, the central stitching zone may be less porous or less rugged than the reinforcing zones 322A, 322B. In one embodiment, the stitching zone 320 desirably includes a pressure sensitive adhesive on a wound-facing face of the reinforcing incision drape 302. In one embodiment, the reinforcing zones 322A, 322B may also include a pressure sensitive adhesive on the wound-facing face of the reinforcing incision drape 302.

In one embodiment, the reinforcing incision drape 302 preferably includes a plurality of pores extending through the reinforcing incision drape that desirably enable medical personnel to have visibility through the drape for observing an underlying incision and/or the tissue surrounding a planned incision. In one embodiment, the plurality of openings that extend through the reinforcing incision drape preferably enable an adhesive to be passed through the openings for forming a strong bond between the reinforcing incision drape and the underlying fragile tissue. In one embodiment, the porous openings are located within the first and second reinforcing zones 322A, 322B, and the stitching zone 320 may be less porous or non-porous. In one embodiment, the porous openings are located within the first and second reinforcing zones 322A, 322B and not within the stitching zone 320. In one embodiment, the porous openings within the first and second reinforcing zones 322A, 322B are larger than the porous openings in the stitching zone 320. In one embodiment, the openings or pores in the surgical mesh have a diameter of about 1 mm.

In one embodiment, the reinforcing incision drape may be a surgical mesh. In one embodiment, the surgical mesh may be a polypropylene mesh. In one embodiment, the surgical mesh may include a substantially flat monofilament polypropylene mesh with reinforcement filaments. The length of the reinforcing incision drape may vary depending upon surgical needs.

In one embodiment, prior to making an incision, the bottom surface of the reinforcing incision drape may be positioned against the fragile tissue of a patient. The bottom surface may have a slight or weak adhesive layer (e.g., a pressure sensitive adhesive) applied thereto for forming a non-permanent and/or repositionable frictional engagement between the reinforcing incision drape and the fragile tissue. Due to the slight or weak adhesive layer, if an initial positioning of the reinforcing incision drape on a patient's fragile tissue is not acceptable (e.g. misaligned), the reinforcing incision drape 302 may be lifted or peeled away from the patient's fragile tissue for re-positioning. Once medical personnel are satisfied that the reinforcing incision drape has been properly positioned and/or aligned atop the fragile tissue (e.g. properly aligned with a surgical site where an incision will be made), a stronger adhesive, such as a clear or translucent adhesive may be applied over the top surface of the reinforcing incision drape for passing through the plurality of openings (e.g., pores) to more permanently and/or more firmly affix the reinforcing incision drape to the fragile tissue. In one embodiment, the clear or translucent adhesive preferably includes tissue glue such as Cyanoacrylate.

In one embodiment, a reinforcing incision drape may be wound into a roll for shipment and storage. In one embodiment, after a surgeon determines a length of an incision required for a surgical procedure, the surgeon may unwind the roll and cut a section of the roll to provide a section of reinforcing incision drape having a desired length. In one embodiment, medical personnel may unwind a section of the reinforcing incision guide onto a flat support surface. In one embodiment, when the reinforcing incision drape has been unwound, a cutting instrument may be used for cutting the reinforcing incision drape to a desired length. In one embodiment, a plurality of reinforcing incision drapes having different sizes, dimensions and/or lengths may be provided to medical personnel. In one embodiment, medical personnel may select one of the reinforcing incision drapes having the proper size, length and/or width that suit the particular surgical needs of a patient. In one embodiment, a plurality of reinforcing incision drapes having different sizes, lengths and/or widths may be provided, and a surgeon may cut or trim a selected one of the plurality of drapes to suit surgical requirements.

In one embodiment, the pressure sensitive adhesive enables the reinforcing incision drape 302 to be initially positioned over a surface of fragile tissue. If a surgeon determines that the reinforcing incision drape 302 is not properly positioned over the fragile tissue, the pressure sensitive adhesive enables the reinforcing incision drape to be removed from the surface of the fragile tissue and re-positioned over the fragile tissue. In one embodiment, after a surgeon is satisfied that the reinforcing incision drape has been properly positioned over the fragile tissue, a stronger and/or more rugged second adhesive may be used to more permanently secure the reinforcing incision drape 302 to the fragile tissue. In one embodiment, the stronger adhesive is applied to the reinforcing zones 322A and 322B of the reinforcing incision drape 302 and is not applied to the stitching zone 320 of the reinforcing incision drape 302.

Figure 3B:
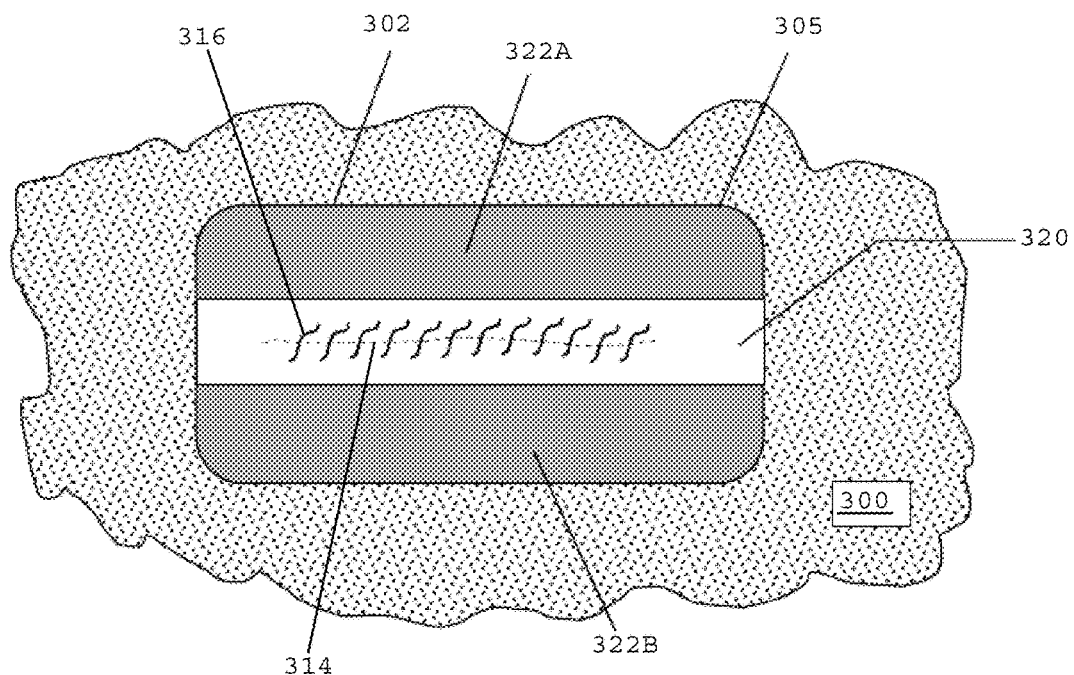
FIG. 3B shows the reinforcing incision drape of FIG. 3A positioned over fragile tissue, in accordance with one embodiment of the present patent application.

Referring to FIG. 3B, in one embodiment, after the reinforcing incision drape 302 has been positioned over a surgical site on the fragile tissue 300, an outer perimeter 305 of the reinforcing incision drape 302 desirably surrounds an area where the incision 314 is to be formed. The stitching zone 320 of the reinforcing incision drape 302 is desirably aligned with and bounds the incision 314.

In one embodiment, the stitching zone 320 is secured to the fragile tissue 300 using only a pressure sensitive adhesive provided on the tissue facing face of the reinforcing incision drape. In one embodiment, the reinforcing zones 322A, 322B also include a pressure sensitive adhesive for adhering the reinforcing incision drape 302 to the fragile tissue. In one embodiment, additional adhesive is applied over the reinforcing zones 322A, 322B of the reinforcing incision drape 302. In one embodiment, the additional adhesive preferably passes through pores provided in the reinforcing zones 322A, 322B for forming a stronger bond between the reinforcing zones 322A, 322B and the fragile tissue 300. In one embodiment, the stitching zone 320 portion of the reinforcing incision drape 302 is less porous than the reinforcing zones 322A, 322B of the reinforcing incision drape 302. In one embodiment, the stitching zone 320 does not include any of the stronger, second adhesive used to bond the reinforcing zones 322A, 322B to the fragile tissue 300.

In one embodiment, a cutting tool, such as a scalpel, may be used for forming an incision 314 in the stitching zone 320 of the reinforcing incision drape 302. The incision 314 preferably extends into the fragile tissue 300 for enabling a surgical procedure to be performed through the incision 314. In one embodiment, at the conclusion of a surgical procedure through the incision 314, a surgical suture 316 may be utilized for closing the incision 314 in the fragile tissue 100 and approximating the cut opposing edges of the reinforcing incision drape 302.

Figure 4:
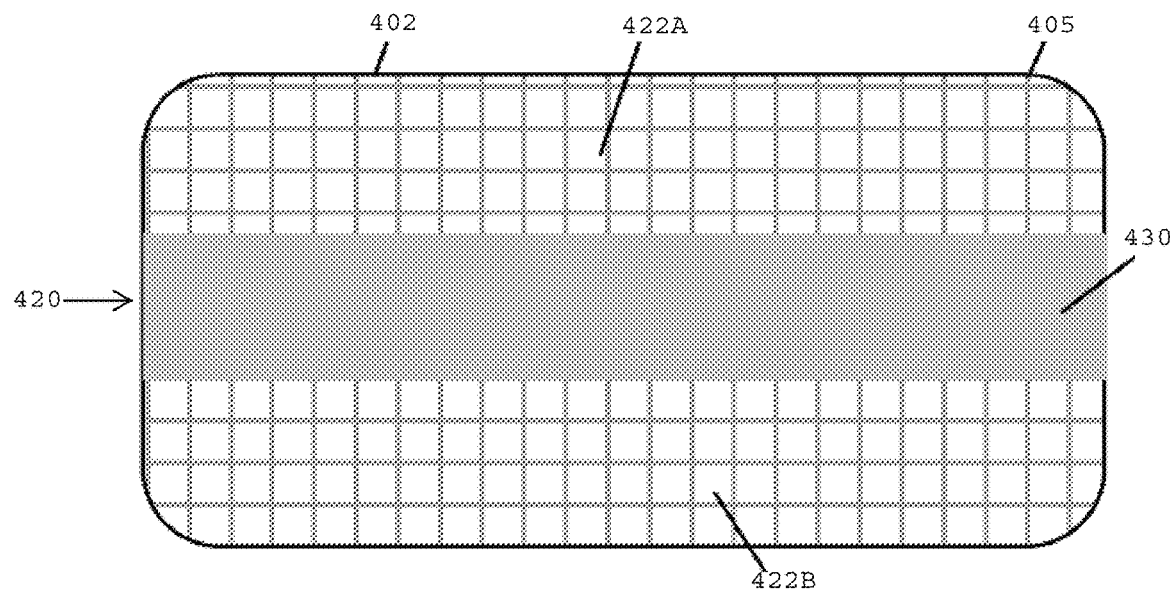
FIG. 4 shows a top plan view of a reinforcing incision drape having a removable liner, in accordance with another embodiment of the present patent application.

Referring to FIG. 4, in one embodiment, a reinforcing incision drape 402 preferably includes an absorbable, porous surgical mesh having an outer perimeter 405 that is adapted to bound a surgical site that has been identified on fragile tissue. In one embodiment, the reinforcing incision drape 402 preferably includes a central stitching zone 420 and two outer reinforcing zones 422A, 422B that bound opposite sides of the central stitching zone 420. The central stitching zone may extend along the length of the reinforcing incision drape 402. In one embodiment, a removable liner 430 preferably overlies a top surface of the central stitching zone 420, whereby the top surface of the stitching zone faces away from a wound-facing side of the reinforcing incision drape 402.

In one embodiment, the reinforcing incision drape 402 preferably includes pressure sensitive adhesive applied over the wound-facing side of the reinforcing incision drape 402.

In one embodiment, after the reinforcing incision drape 402 is positioned over the fragile tissue and with the removable liner 430 in place over the top surface of the stitching zone, a second, stronger liquid adhesive may be applied to the top surface of the reinforcing incision drape 402 that faces away from the fragile tissue. The stronger liquid adhesive preferably passes through the pores located in the reinforcing zones 422A, 422B of the reinforcing incision drape 402. The releasable liner 430 acts as a mask to prevent the stronger liquid adhesive from contacting the stitching zone 420 of the reinforcing incision drape 402. In one embodiment, after the stronger liquid adhesive applied to the reinforcing zones 422A, 422B has cured and/or hardened, the releasable liner 430 may be removed for exposing the top surface of the stitching zone 420. An incision may be formed in the stitching zone 420 of the reinforcing incision drape for making a surgical opening in the fragile tissue. At the conclusion of a surgical procedure, the incision may be closed using surgical closing components, such as surgical sutures.

Figure 5:
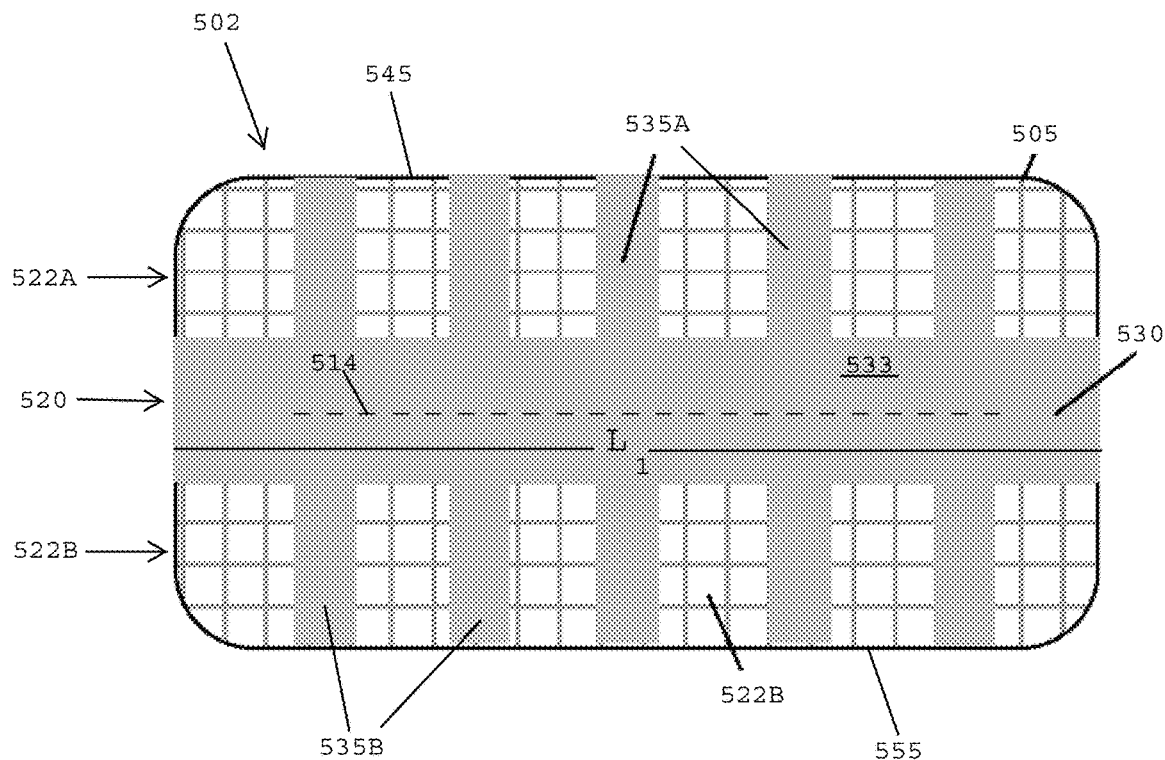
FIG. 5 shows a top plan view of a reinforcing incision drape having a removable liner, in accordance with still another embodiment of the present patent application.

Referring to FIG. 5, in one embodiment, a reinforcing incision drape 502 is desirably adapted to cover a surgical site on a surface of fragile tissue. In one embodiment, the reinforcing incision drape 502 has an outer perimeter 505 that is adapted to bound a surgical site on the fragile tissue. The reinforcing incision drape 502 may be made of a porous surgical mesh. In one embodiment, the reinforcing incision drape 502 desirably has a central stitching zone 520 and first and second reinforcing zones 522A, 522B that are located on opposite sides of the central stitching zone 520. The central stitching zone 520 and the first and second reinforcing zones 322A, 322B preferably extend along the length $L_1$ of the reinforcing incision drape 502. In one embodiment, the reinforcing incision drape 502 includes a releasable liner 530 that preferably extends over top surface of the central stitching zone 520, the top surface of the stitching zone facing away from the wound-facing side of the reinforcing incision drape. In one embodiment, the releasable liner 530 has laterally extending strips 535A, 535B that extend laterally from a central section 533 to lateral side edges 545, 555 of the drape 502. In one embodiment, the spaced sections of first reinforcing zone 522A are preferably exposed between the first laterally extending strips 535A, and spaced sections of the second reinforcing zone 522B are preferably exposed between the second laterally extending strips 535B.

In one embodiment, after the reinforcing incision drape 502 has been initially positioned over the fragile tissue, a liquid adhesive may be applied to the exposed surface areas of the reinforcing incision drape 502 that are not covered by the releasable liner 530. The liquid adhesive desirably passes through the pores in the first and second reinforcing zones 522A, 522B that are not covered by the respective laterally extending strips 535A, 535B. The stronger liquid adhesive that passes through the exposed pores is desirably cured for strongly adhering the first and second reinforcing zones 522A, 522B to the exposed surface of the fragile tissue. After the stronger adhesive has cured, the releasable liner 530 including the laterally extending strips 535A, 535B may be removed from the exposed top surface of the reinforcing incision drape 502.

In one embodiment, an incision 514 may be made in the reinforcing incision drape 502. The incision 514 preferably extends along the length of the central stitching zone 520 of the reinforcing incision drape for providing access to a surgical site within the fragile tissue. The incision 514 preferably extends into the fragile tissue. After a surgical procedure has been completed, a closure element such as surgical sutures may be used for closing the incision 514 formed in the stitching zone 520 and the fragile tissue.

Figure 6A:
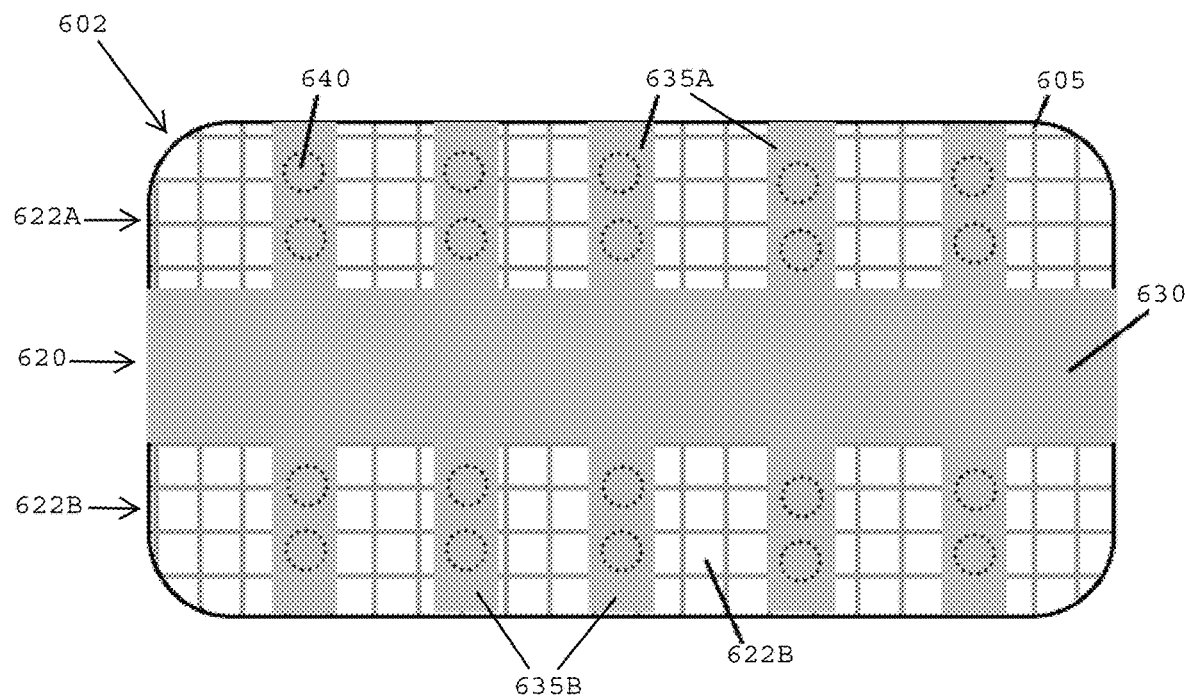
FIG. 6A shows a top plan view of a reinforcing incision drape having a removable liner, in accordance with yet another embodiment of the present patent application.

Referring to FIG. 6A, in one embodiment, a reinforcing incision drape 602 preferably has an outer perimeter 605 that defines a length and a width of the reinforcing incision drape. In one embodiment, the reinforcing incision drape 602 preferably includes a porous surgical mesh having pores extending between a top surface and a bottom surface of the surgical mesh. In one embodiment, the surgical mesh may be absorbable. In one embodiment, a bottom major face of the surgical mesh includes a pressure sensitive adhesive that enables the reinforcing incision drape 602 to be releasably secured to the tissue. In one embodiment, the pores formed in the surgical mesh enable an adhesive, such as a liquid adhesive, to pass through the pores for forming a stronger, more permanent bond between the reinforcing incision drape 602 and the underlying fragile tissue.

In one embodiment, the reinforcing incision drape 602 desirably includes a central stitching zone 620 that is bounded by first and second reinforcing zones 622A, 622B. In one embodiment, the reinforcing incision drape 602 desirably includes a releasable liner 630 having a central section 633 that preferably overlies and extends along the length of the central stitching zone 620 and first and second laterally extending strips 635A, 635B that extend outwardly from opposite sides of the central section 633 of the releasable liner 630.

In one embodiment, the reinforcing incision drape 602 desirably has relatively large openings 640 (i.e., larger than the pores) that are initially covered by the laterally extending strips 635A, 635B of the releasable liner 630. In one embodiment, the laterally extending strips 635A, 635B of the releasable liner 630 cover the relatively large openings 640. In one embodiment, the first laterally extending strips 635A of the releasable liner are spaced from one another so that at least some of the pores in the first reinforcing zone 622A of the reinforcing incision drape 602 are exposed between the first laterally extending strips 635A. In one embodiment, the second laterally extending strips 635B are spaced from one another so that at least some of the pores in the second reinforcing zone 622B of the reinforcing incision drape 602 are exposed between the second laterally extending strips 635B.

In one embodiment, after the tissue-facing surface of the reinforcing incision drape 602 is positioned over fragile tissue, and with the releasable liner 630 in place over the top surface of the reinforcing incision drape 602, a liquid adhesive 625 (FIG. 6B) may be applied over a top surface of the reinforcing incision drape 602. The liquid adhesive desirably passes through the exposed porous sections of the first and second reinforcing zones 622A, 622B that lie between the respective first and second laterally extending strips 635A, 635B.

Figure 6B:
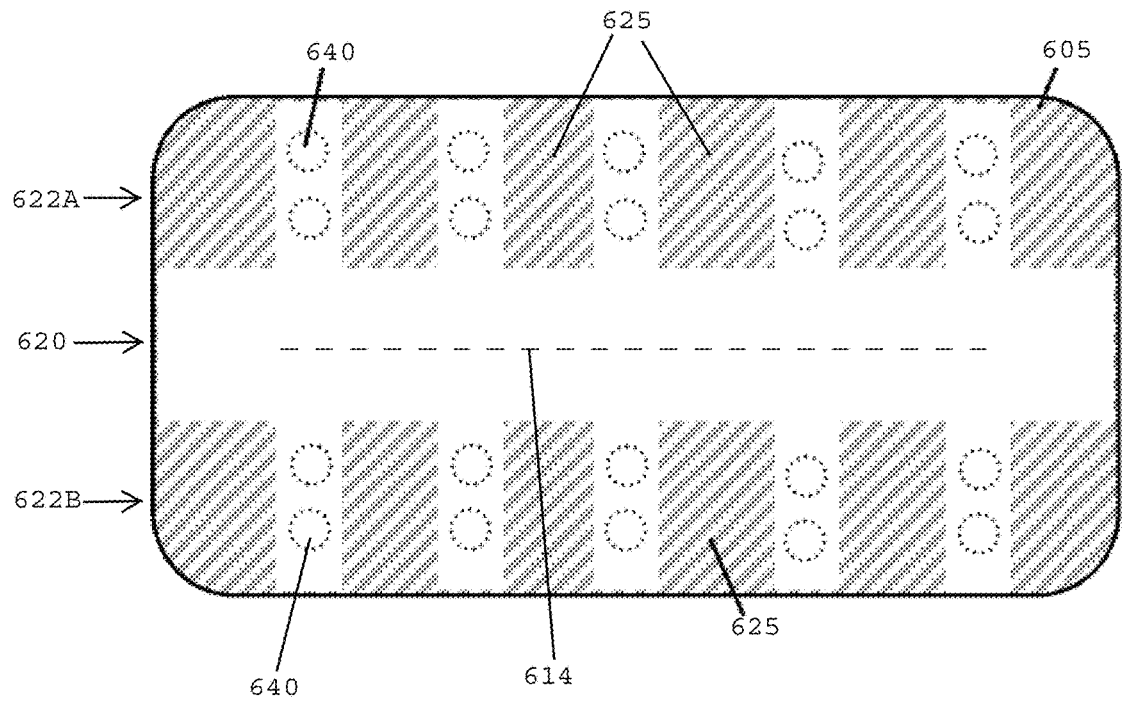
FIG. 6B shows the reinforcing incision drape of FIG. 6A after the removable liner has been stripped away to expose sections of the reinforcing incision drape, in accordance with one embodiment of the present patent application.
Figure 7:
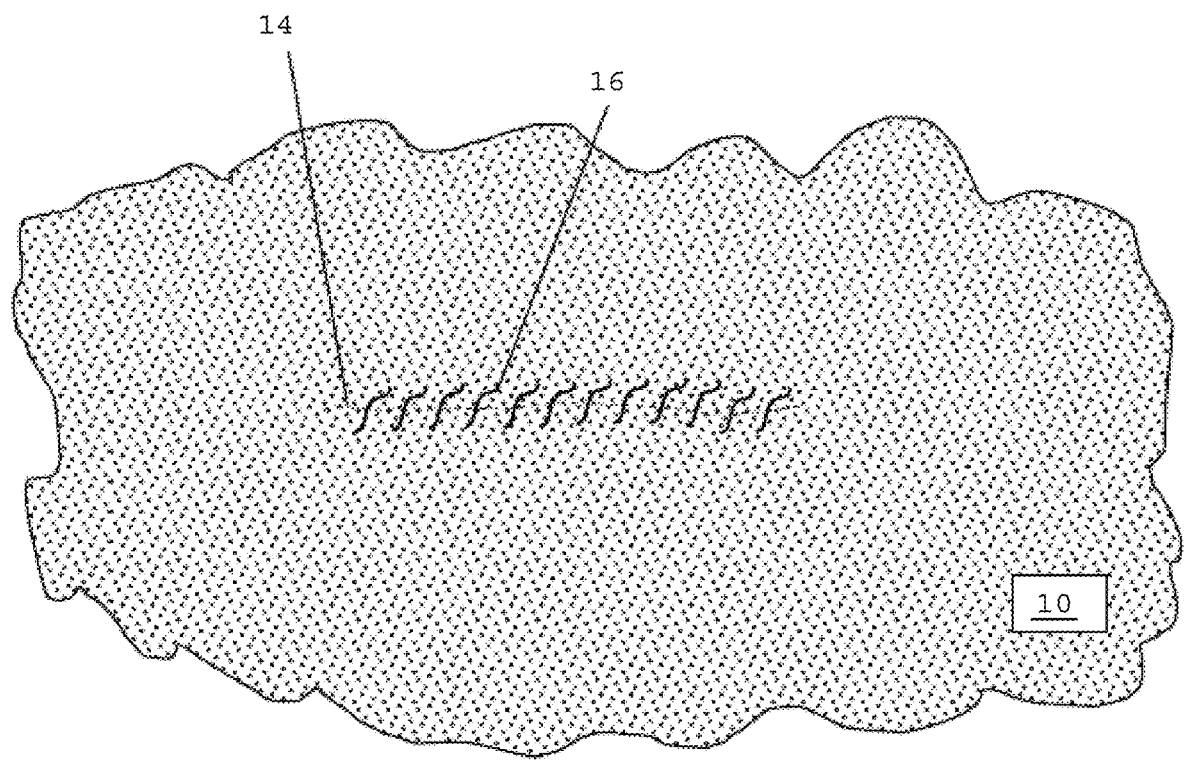
FIG. 7 shows a prior art method of closing a wound formed in fragile tissue.

Referring to FIGS. 6A and 6B, in one embodiment, after the liquid adhesive 625 cures, the releasable liner 630 including the laterally extending strips 635A, 635B may be removed from the top surface of the reinforcing incision drape 602. After the liner 630 has been removed, the central stitching zone 620 and the openings 640 previously covered by the first and second laterally extending strips 635A, 635B are exposed. The cured adhesive 625 extends over the first and second reinforcing zones 622A, 622B and between the opening 640 and the areas previously covered by the laterally extending strips 635A, 635B (FIG. 6A). An incision 614 may be created in the stitching zone 620 of the reinforcing incision drape 602 and into fragile tissue underlying the reinforcing incision drape. At the conclusion of a surgical procedure, the incision in the fragile tissue and the reinforcing incision drape may be closed using a tissue closing component such as sutures, absorbable sutures, tacks, staples and/or tissue adhesive. The reinforced incision drape preferably supports the fragile tissue during suturing and healing for preventing the fragile tissue from being damaged by the sutures.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A method of reinforcing subcutaneous fragile tissue comprising:
    obtaining a reinforcing incision drape having top and bottom major faces;
    using an adhesive for directly adhering said bottom major face of said reinforcing incision drape to subcutaneous fragile tissue;
    creating an incision through said reinforcing incision drape and into said subcutaneous fragile tissue;
    performing a surgical procedure through said incision;
    passing a surgical closing component through said reinforcing incision drape and said subcutaneous fragile tissue for closing said incision.

2. The method as claimed in claim 1, wherein said reinforcing incision drape, said adhesive and said surgical closing component are absorbable.

3. The method as claimed in claim 1, wherein said reinforcing incision drape comprises an absorbable surgical mesh, said adhesive comprises absorbable adhesive, and said surgical closing component comprises an absorbable suture.

4. The method as claimed in claim 1, wherein said reinforcing incision drape comprises:
    a centrally located stitching zone;
    first and second reinforcing zones that extend along opposite sides of said centrally located stitching zone, wherein said centrally located stitching zone has different structural properties than said first and second reinforcing zones.

5. The method as claimed in claim 4, wherein said first and second reinforcing zones are more porous than said centrally located stitching zone.

6. The method as claimed in claim 5, wherein the using an adhesive step comprises:
    using a weaker adhesive for securing said centrally located stitching zone to said subcutaneous fragile tissue; and
    using a stronger adhesive for securing said first and second reinforcing zones to said subcutaneous fragile tissue.

7. The method as claimed in claim 6, wherein said stronger adhesive comprises an absorbable adhesive containing a cross-linking initiator.

8. The method as claimed in claim 7, wherein said stronger adhesive comprises cyanoacrylate.

9. The method as claimed in claim 6, further comprising after the using a weaker adhesive step, applying said stronger adhesive over said top surface of said reinforcing incision drape and within said first and second reinforcing zones of said reinforcing incision drape.

10. The method as claimed in claim 9, further comprising:
    obtaining a releasable liner over said top surface of said reinforcing incision drape within said stitching zone of said reinforcing incision drape, wherein said releasable liner covers said stitching zone during the applying said stronger adhesive step;
    after the applying said stronger adhesive step, removing said releasable liner from said top surface of said reinforcing incision drape for exposing said stitching zone at said top surface of said reinforcing incision drape.

11. The method as claimed in claim 4, wherein said creating an incision step comprises forming an incision in said stitching zone of said reinforcing incision drape and said subcutaneous fragile tissue underlying said stitching zone, and wherein said passing a surgical closure step comprises passing a surgical suture through said stitching zone of said reinforcing incision drape and said subcutaneous fragile tissue underlying said reinforcing incision drape.

12. The method as claimed in claim 1, wherein said surgical closing component is selected from the group consisting of sutures, barbed sutures, surgical staples and surgical adhesives.

13. The method as claimed in claim 1, wherein after the using an adhesive for directly adhering said bottom major face of said reinforcing incision drape to subcutaneous fragile tissue, said bottom major face of said reinforcing incision drape is in contact with said subcutaneous fragile tissue.

14. A method of reinforcing subcutaneous fragile tissue comprising:
   obtaining an absorbable surgical mesh having top and bottom major surfaces, said absorbable surgical mesh including a stitching zone and first and second reinforcing zones that bound opposite sides of said stitching zone;
   making an incision in a patient's skin for exposing subcutaneous fragile tissue;
   using one or more absorbable adhesives for directly adhering said bottom major surface of said absorbable surgical mesh to said subcutaneous fragile tissue;
   creating an incision through said stitching zone of said absorbable surgical mesh that is directly adhered to said subcutaneous fragile tissue and into said subcutaneous fragile tissue;
   performing a surgical procedure through said incision;
   passing an absorbable suture through said stitching zone of said absorbable surgical mesh that is directly adhered to said subcutaneous fragile tissue and said subcutaneous fragile tissue for closing said incision.

15. The method as claimed in claim 14, wherein the using one or more absorbable adhesives step comprises:
   using a weaker absorbable adhesive for adhering said stitching zone of said absorbable surgical mesh to said subcutaneous fragile tissue;
   using a stronger absorbable adhesive for adhering said first and second reinforcing zones of said absorbable surgical mesh to said subcutaneous fragile tissue.

16. The method as claimed in claim 15, wherein the using a stronger absorbable adhesive step comprises:
   after placing a bottom surface of said absorbable surgical mesh in contact with said subcutaneous fragile tissue, applying said stronger absorbable adhesive over said top major surface of said absorbable surgical mesh and within said first and second reinforcing zones of said absorbable surgical mesh.

17. The method as claimed in claim 16, further comprising:
   obtaining a releasable liner that covers said top major surface of said absorbable surgical mesh within said stitching zone;
   after the applying said stronger absorbable adhesive over said top major surface of said absorbable surgical mesh step, removing said releasable liner for uncovering said stitching zone at said top major surface of said absorbable surgical mesh.

18. The method as claimed in claim 14, wherein said stitching zone of said absorbable surgical mesh is less porous than said first and second reinforcing zones of said absorbable surgical mesh.

19. The method as claimed in claim 14, wherein after the using one or more absorbable adhesives for directly adhering said bottom major surface of said absorbable surgical mesh to said subcutaneous fragile tissue, said bottom major surface of said absorbable surgical mesh is in contact with said subcutaneous fragile tissue.

20. A method of reinforcing subcutaneous fragile tissue comprising:
   obtaining an absorbable surgical mesh having top and bottom major surfaces, said absorbable surgical mesh including a stitching zone and first and second reinforcing zones that bound opposite sides of said stitching zone, wherein said stitching zone of said absorbable surgical mesh is less porous than said first and second reinforcing zones of said absorbable surgical mesh;
   making an incision in a patient's skin for exposing subcutaneous fragile tissue;
   using one or more absorbable adhesives for adhering said bottom major surface of said absorbable surgical mesh to said subcutaneous fragile tissue;
   creating an incision through said stitching zone of said absorbable surgical mesh and into said subcutaneous fragile tissue;
   performing a surgical procedure through said incision;
   passing an absorbable suture through said stitching zone of said absorbable surgical mesh and said fragile tissue for closing said incision.

* * * * *